United States Patent [19]
Hartig et al.

[11] 4,122,286
[45] Oct. 24, 1978

[54] MANUFACTURE OF GLYCOL ESTERS

[75] Inventors: Juergen Hartig, Ludwigshafen; Hans-Martin Weitz, Bad Durkheim, both of Fed. Rep. of Germany

[73] Assignee: BASF Aktiengesellschaft, Ludwigshafen, Fed. Rep. of Germany

[21] Appl. No.: 792,697

[22] Filed: May 2, 1977

[30] Foreign Application Priority Data

May 8, 1976 [DE] Fed. Rep. of Germany ....... 2620444
Aug. 14, 1976 [DE] Fed. Rep. of Germany ....... 2636670

[51] Int. Cl.$^2$ .............................................. C07C 67/05
[52] U.S. Cl. .............................. 560/246; 252/431 R; 252/431 C; 260/410.6; 560/1; 560/198; 560/224

[58] Field of Search ................... 560/246, 1, 198, 224; 260/410.6

[56] References Cited

U.S. PATENT DOCUMENTS 4,069,381   1/1978   Gaenzler .............................. 560/246

Primary Examiner—James O. Thomas, Jr.
Assistant Examiner—Michael Shippen
Attorney, Agent, or Firm—Keil, Thompson & Shurtleff

[57] ABSTRACT 1,2-Glycol esters are obtained particularly advantageously, by reacting an olefin with molecular oxygen and a carboxylic acid, if a reaction product of o-titanic acid with low molecular weight alcohols or carboxylic acids, e.g. dititanium hexaacetate, is used as the catalyst.

3 Claims, No Drawings

MANUFACTURE OF GLYCOL ESTERS

The present invention relates to a process for the manufacture of glycol esters by reacting an olefin with molecular oxygen and a carboxylic acid in the presence of a novel catalyst system.

This method of manufature of glycol esters (in practice the acetates of ethylene glycol and of 1,2-propylene glycol are obtained in this way) has been disclosed, as have various catalysts for the reaction.

According to French Pat. No. 1,421,288, a bromide, in the presence or absence of a metal salt, may be used; the solvent is a mixture of the carboxylic acid with an aromatic hydrocarbon.

According to French Pat. No. 1,419,966, noble metals of group VIII of the periodic table of the elements are used, with nitric acid or nitrates serving as oxygen donors or oxidizing agents.

U.S. Pat. No. 3,542,857 discloses the use of cerium salts which are soluble in carboxylic acids, as catalysts.

U.S. Pat. No. 3,262,969 discloses the catalytic action of redox systems which contain alkali metal halides and palladium salts.

German Laid-Open Application DOS No. 1,931,563 discloses iodine and iodine compounds of cations of heavy metals or alkali metals as catalysts for the process in question. The usefulness of bromine or chlorine in a similar system which furthermore contains metal cations which can exist in several valencies (eg. tellurium, cerium, arsenic, antimony, manganese and cobalt) has also been disclosed. Further comparable systems are disclosed in German Laid-Open Application DOS No. 2,126,505 and British Pat. No. 1,058,995. It appears that of the above catalyst systems those containing tellurium and bromine have, for various reasons, the best prospects of industrial usefulness; however, a disadvantage of these systems, apart from the corrosiveness of the reaction mixtures, is that, for example, substantial amounts of bromine are lost unless considerable efforts are made to recover bromine-containing by-products (cf. U.S. Pat. No. 3,884,965). Furthermore, halogen-containing by-products lower the yield since they can, in some cases, not be converted to the desired products.

Another catalyst system, which apparently avoids these disadvantages, is disclosed in German Laid-Open Application DOS No. 2,260,822 and British Pat. Nos. 1,441,869 and 1,441,160. This comprises certain complex compounds of certain rare transition metals, from amongst zirconium, hafnium, niobium, tantalum, molybdenum, tungsten and rhenium, with, for example, alkali metals, titanium, vanadium, chromium, manganese, iron, cobalt, nickel, copper, zinc, aluminum or silver. German Laid-Open Application DOS No. 2,260,822 is particularly significant in this context. From this publication, it may be assumed that the catalysts which favor the oxidation of the olefins are polynuclear complex compounds wherein the central atom is an atom of the above elements. This assumption is based on concepts of polynuclear complexes of different compositions and exhibiting different catalytic activity. According to the views expressed in the said publication, the halogens, especially fluorine, chlorine and bromine, play a preferred role in the formation of such catalytically active polynuclear complexes.

However, because of the evidently unavoidable presence of halogens, all these catalysts are very corrosive and we have found that the reaction mixtures formed can only be handled in vessels made from, for example, tantalum, titanium, Hastelloy and other highly resistant materials of construction. Furthermore, the process is rather non-specific and numerous olefin oxidation products, eg. methyl acetate, acetaldehyde, isopropyl acetate and the like, are formed, thereby counterbalancing the inherently low costs of the catalysts.

It is an object of the present invention to provide a catalyst system which does not suffer from the above disadvantages, or only exhibits them to a substantially lesser degree. We have found that this object is achieved and that the manufacture of 1,2-glycol esters by reacting an olefin with molecular oxygen and a carboxylic acid in the presence of a catalyst can be carried out with high selectivity and at high rates, If the catalyst used is a compound of o-titanic acid with a preferably low molecular weight alcohol and/or with a preferably low molecular weight carboxylic acid. The compound can be used by itself or supported on a carrier.

The compounds may be obtained, for example, by reacting halides of 4-valent titanium and/or esters of titanic acid, but preferably $TiCl_4$, with a monohydric or polyhydric alcohol or with a mixture of an anhydride of a monobasic or polybasic carboxylic acid with the carboxylic acid or with the anhydride alone; the use of acetic acid and/or acetic anhydride is preferred, since in general the acetates are, in practice, the most important products to be obtained by the new process. The compounds will also form in the reaction mixture, which contains acid, if titanic acid is added thereto.

The molar ratios of titanium compound to carboxylic acid or carboxylic anhydride to be used in manufacturing the catalyst are, for example, from 1:4 to 1:10, and do not appear to be critical, particularly since it is not essential to remove any excess carboxylic acid.

The above reactions as a rule take place spontaneously at from 0° to 200° C. or even below and above the stated range.

The catalysts of the invention are generally known as compounds per se; according to ideas put forward in the literature, they have, for example, the structure $(Ti(OR^1)_4$, where $R^1$ is alkyl of, for example, 1 to 20 carbon atoms or two radicals $R^1$ together form a divalent alkylene radical (in the case of glycol esters). Titanium tetrabutylate and titanium diglycolate may be mentioned as examples.

The catalysts may also be (mixed) ester-anhydrides, eg. of the formula $(Ti(OR^1)_m(OAc)_n$, where $R^1$ has the above meaning, Ac is an acyl radical of a carboxylic acid and $m$ and $n$ together are 4, and each may be an integer from 1 to 3. The carboxylic acid may be monobasic or polybasic, saturated or olefinically unsaturated. In general, suitable carboxylic acids are of 1 to 20 carbon atoms, especially of 2 to 10 carbon atoms.

Further suitable catalysts are mixed anhydrides of o-titanic acid with a carboxylic acid; these are in some cases particularly active. For steric reasons, they frequently are not known as symmetrically tetrasubstituted compounds and instead have, for example, the formula $(AcO)_3Ti-O-Ti(OAc)_3$, where Ac has the above meaning, preferably acetyl.

In general, the catalysts are evidently esters, ester-anhydrides or mixed anhydrides of o-titanic acid and a carboxylic acid. They could also reasonably be described as basic titanates of a carboxylic acid. Reference may be made, in this context, to an article by Pande and Mehrotra in J. Prakt. Chem., 5, (1958), 101 et seq. Valuable information may also be found in M. Gina and E. Monath, Z. anorg. Chem. 143 (1925), 383 et seq.; A.

Rosenheim and O. Schütte, Z. anorg. Chem. 26 (1960), 252; Gmelin, Handbuch der anorg. Chemie, Volume 41, page 371 et seq; Chemistry and Industry 1958 (Sept. 13), pages 1,198–99; Z. anorg. Chem. 290 (1957), 87 and J. Am. Chem. Soc. 79 (1957), 4,344, which are herein incorporated by reference.

It is true that like the systems previously disclosed, which contain titanium, the catalysts according to the invention in some cases contain two central metal atoms, but nowhere has this relationship, and in particular the exceptionally good activity of the catalyst according to the invention, been pointed out.

If it is intended to use a catalyst which has been obtained by applying a compound of o-titanic acid with a low molecular weight alcohol and/or with a low molecular weight carboxylic acid to a solid carrier, the inherently soluble compounds which are obtained by reacting halides and/or esters of tetravalent titanium (preferably $TiCl_4$) with a monohydric or polyhydric alcohol or with an anhydride of a monobasic or polybasic carboxylic acid, alone or together with the carboxylic acid, may be fixed to a carrier.

Suitable carriers for the manufacture of the solid catalysts, on which the soluble compounds are, for example, adsorbed, are generally known; they include, for example, carriers based on active charcoal (surface area of the order of magnitude of 1,000 $m^2/g$), silica gel ($\sim$250 $m^2/g$) or alumina ($\sim$0.5 $m^2/g$). Other solid oxides, phosphates, silicates, tungstates and, for example, solid heretopolyacids, which are insoluble in the reaction mixture, may also be used. In our experience the chemical nature of the carrier, and whether the soluble compounds are merely adsorbed or form a chemical compound with the carrier, matters little.

Solid catalysts may be obtained, for example, by suspending the carrier in a suitable solution of the titanium compounds, evaporating the suspension to dryness and washing it, if appropriate, with a suitable wash liquid. In this process, the carrier is obviously impregnated with the catalyst solution; however, to save material it is frequently also possible to spray the cold or hot catalyst carrier with a suitable solution, whereupon a catalytically active layer forms on the surface of the carrier.

The solid catalyst releases virtually no soluble material into the strongly acid reaction mixture.

It is surprising that the adsorbed catalyst has the same action as if it were in the dissolved state.

Like the conventional processes, the process of the invention takes place at an elevated temperature, advantageously at from 50° to 200° C. It is also possible to work below or above the said temperature range, if, respectively, a low rate of reaction or more expensive apparatus can be tolerated.

It will be clear that the process of the invention is advantageously carried out under pressure in order to achieve satisfactory conversions and yields. If the process is carried out batchwise, the minimum pressure to be used is substantially fixed by the amount of olefin and oxygen to be introduced into the reaction mixture and by the reaction temperature used. If the process is carried out continuously, it has proved advantageous to allow the reaction to take place at pressures of from about 10 to 100 bars. It is however possible to work below or above this range, with similar provisos to those made in connection with the choice of a suitable temperature.

The catalytically active amount of the catalyst may vary with wide limits and is, for example, from $10^{-3}$ to 0.2 mole/mole of olefin. Whether the amount used is catalytically active can in each case be discerned from the outcome of the reaction.

The new catalyst has substantial advantages since it is neither corrosive nor expensive and furthermore gives a substantial reaction rate. In addition, it gives an excellent selectivity, not previously observed. (Selectivity in this context means the molar ratio of the desired reaction products to the total reaction products).

Amongst the olefins which may be used to carry out the process according to the invention, ethylene and propylene have hitherto occupied a preferred position because of the commercial importance of the end products; however, in principle higher olefins can be converted to the corresponding glycol esters by a similar reaction. It is true that in principle all low molecular weight carboxylic acids may be used as carboxylic acids for the purposes of the invention; however, because of the importance of the acetates and the fact that the esters, for their part, are in many cases merely intermediates, the process is in the majority of cases carried out with acetic acid. The resistance to oxidation at the reaction temperature is in general a criterion of the suitability of a carboxylic acid; furthermore, the acid should, for practical reasons, be liquid at a temperature between room temperature and the reaction temperature. Examples of carboxylic acids which are suitable from these points of view are fatty acids, dibasic aliphatic carboxylic acids and olefinically unsaturated carboxylic acids. Specific examples are acetic acid, propionic acid, butyric acid, pivalic acid, methacrylic acid, cyclohexenecarboxylic acid and heptadecanedicarboxylic acid. Where the catalyst is a mixed acid anhydride, it preferably contains the same carboxylic acid.

It is true that in general the carboxylic acid itself will be used as the solvent for carrying out the reaction; in special cases, however, it is possible to use an oxidation-resistant auxiliary solvent, eg. an aromatic hydrocarbon. The end products formed may in principle also be used as solvents.

The reaction mixture may in addition contain by-products which are formed in the reaction and are isolated in the course of subsequent working-up and recycled. Examples of such by-products are allyl acetate and isopropyl acetate, which are formed on oxidative acetylation of propylene. By recycling such products, the overall yield of the process of the invention can of course be improved.

The glycol esters which may be manufactured according to the invention are conventionally used extensively as intermediates, solvents and plasticizers. Glycol esters of higher carboxylic acids are of value as surfactants.

Since the hydrolysis of the esters generally takes place smoothly and simply, the glycols on which the esters are based also become accessible by the new process. In this case, the acid liberated by hydrolysis may be recycled to the process. According to an unpublished proposal, the acid may be recycled in the form of an ester instead of as the free acid, in which case it is merely necessary to ensure that the reaction mixture possesses hydrolytic properties and is capable of releasing free carboxylic acid for carrying out the reaction.

The process can of course be carried out batchwise or continuously and in this way any installation of the prior art may be utilized.

In the Examples which follow, amounts are by weight, unless stated otherwise.

EXAMPLE 1

600 g of acetic acid, 4.66 g of a compound which has been obtained by reacting titanium tetrachloride, acetic acid and acetic anhydride and which, according to its analysis, has the formula $(AcO)_3TiOTi(OAc)_3$ (where Ac is acetyl) and 146 ml of liquid propylene are introduced into a 2 liter shaking autoclave. 13 liters (S.T.P.) of oxygen are also injected and after heating up in the course of 5 hours, the autoclave is shaken for 3 hours at 160° C. After cooling and letting down, whereupon 31.25 liters (S.T.P.) of gaseous constituents escape, a total of 622.5 g of liquid reaction products is obtained. This material is filtered (leaving a filter residue of 4 g) and is concentrated under reduced pressure on a rotary evaporator.

The residue of 38.9 g is now distilled under reduced pressure (boiling point about 70° C./0.2 mbar). The distillate comprises 88% of propane-1,2-diol diacetate, 10% of propane-1,2-diol 1-monoacetate and 2% of propane-1,2-diol 2-monoacetate.

If the reaction products are subjected to quantitative analysis by gas chromatography before being concentrated, the following composition is found:

acetaldehyde: 0.25% by weight
methyl acetate: 0.80% by weight
i-propyl acetate: 0.09% by weight
allyl acetate: 0.08% by weight
allyl alcohol: 0.007% by weight
propanediol diacetate: 4.36% by weight
propanediol 1-monoacetate: 0.16% by weight
propanediol 2-monoacetate: 0.05% by weight
acetoxymethoxypropane: 0.04% by weight
remainder acetic acid, water and dissolved propylene.

Accordingly, the selectivity is found to be 72 mole %, whilst the space-time yield is 1,830 g of distillate per kg of catalyst per hour.

EXAMPLE 2

The procedure described in Example 1 is followed, but the heating-up time is restricted to 2½ hours. In this case, the selectivity is 86 mole %, the space-time yield being 1,360 g of product per kg of catalyst per hour. It follows from this result that if the heating-up time is shorter, the amount of by-products formed is less, but at the same time the conversion is also less.

EXAMPLE 3

To carry out the process continuously, the following method is used:

The reactor is an internally enamelled pressure-resistant steel tube having an internal width of 25 mm and a length of 2 m. It is packed with hollow spheres of Hastelloy C, a corrosion-resistant metal alloy, and is charged, under a pressure of 30 bars and at an operating temperature of 170° C., with a mixture of acetic acid, propylene, dissolved oxygen and the solution of the catalyst in methanol. The amounts used are from 1.5 to 10 l of acetic acid per hour, from 200 to 800 ml of propylene per hour and from 7 to 30 ml of 35% strength catalyst solution per hour.

The liquid constituents are combined in a continuous mixer, the acetic acid first being fed to an adjustable ejector in order to enable it to become saturated with oxygen. A liquid level regulator ensures that gaseous oxygen cannot be carried with the liquid which leaves the ejector mixer. The other constituents are added, by means of metering pumps, to the homogeneous (ie. gas-free) oxygen-containing solution obtained above, and the mixture is then fed into the reaction chamber under the conditions described. At a solution temperature of 40° C., the device used permits dissolving 0.15 ml (S.T.P.) of oxygen per gram of acetic acid and per bar pressure, and this figure corresponds to the experimentally determined solubility product.

At the stated operating temperature, propylene glycol acetate is obtained in varying amounts depending on the residence time and on the composition of the mixture. In general, the conversion of oxygen is complete. Using 6 l/h of acetic acid, 30 ml of catalyst solution and 500 ml of propylene, a space-time yield of 400 g of acetates per liter of reaction space and per hour is achieved; if the throughput is reduced to 25% (so that the residence time is increased four-fold), a space-time yield of 77 g is achieved.

EXAMPLE 4

600 g of acetic acid, 3.4 g of titanium tetrabutylate and 146 ml of liquid propylene are introduced into the apparatus described in Example 1. 26 liters (S.T.P.) of oxygen are injected and after a heating-up period of 3 hours, the apparatus is shaken for 3 hours at 160° C. 26.8 l (S.T.P.) of gases, containing 2% by volume of oxygen, and 614.8 g of liquid crude product (reaction mixture) are obtained. After working up as described, 16.1 g of distillable high-boiling acetates are obtained, containing 85.3% of propylene glycol diacetate, 12.5% of propylene glycol monoacetate and 2.1% of propylene glycol. The selectivity is found to be 67.3% and the conversion 1,570 g/kg of catalyst.h.

EXAMPLE 5

(a) Manufacture of the catalyst

The compound $Ti_2O(OAc)_6$ (Ac = acetyl) is obtained by the method of manufacture described in J. prakt. Chem.5 (1958), 101 et seq.

The titanium salt formed is dissolved in methanol in a quantity sufficient to give a concentration of 3% of titanium with reference to the carrier used.

2 l of γ-alumina extrudate of 6 mm diameter are introduced into the solution, the methanol is evaporated off and the catalyst is dried in a drying oven under reduced pressure at 100° C. The titanium content is confirmed by analysis.

(b) Process method

The catalyst described above is placed in an enamelled pressure-resistant steel tube having an internal diameter of 50 mm and a length of 1.6 m. Using an operating pressure of 35 bars, at 180° C., the constituents of the reaction mixture, ie. acetic acid, oxygen and propylene, are passed upward through the catalyst bed.

The amounts used are as follows:

The throughput of acetic acid is varied from 1.5 to 10 l/hour; at the same time, the amount of (liquid) propylene is also varied from 200 to 1,000 ml/hour. The acetic acid is in each case saturated with oxygen in a mixing device, before entering the reactor.

An acceptable conversion is achieved at all concentrations and all relative proportions. By way of example, the amounts obtained with a conversion of 5 l of acetic acid and 500 ml of liquid propene/hour are given below. The oxygen conversion under these conditions is about 95%. The data relate to the reaction mixture which has been freed from propylene (the figures in parentheses are percentages by weight after subtracting the acetic acid).

methyl acetate: 0.039 (1.57)
i-propyl acetate: 0.050 (2.01)
i-propanol: —
allyl acetate: 0.022 (0.89)
allyl alcohol: —
propane-1,2-diol diacetate: 1.616 (65.11)
propane-1,2-diol monoacetate: 0.755 (30.42)
propane-1,2-diol: —

The selectivity is calculated to be 85.8 mole percent. The sample was taken after a running period of 26 hours.

EXAMPLE 6

The catalyst is manufactured as described above, but active charcoal is used in place of alumina and before the actual drying the bulk of the methanol is distilled off in a simple distillation apparatus. The material is then dried under reduced pressure at from 60° to 70° C. After drying, the finished catalyst contains 2.7% of titanium.

Two liters of the catalyst manufactured as described were placed in the apparatus described in Example 1, and the unit was operated under a pressure of 30 bars at 180° C., the temperature being the result of external heating.

At an hourly throughput of 4 l of acetic acid saturated with oxygen and 450 ml of liquid propene, the reaction mixture obtained as described above has the composition shown below (the values in parentheses being percentages by weight, leaving the acetic acid out of account):

methyl acetate: 0.029 (3.84)
i-propyl acetate: 0.096 (11.2)
allyl acetate: 0.027 (3.1)
propane-1,2-diol diacetate: 0.426 (49.6)
propane-1,2-diol monoacetate: 0.281 (32.7)

The selectivity is calculated to be 76 mole percent.

We claim:

1. In a process for the manufacture of a 1,2-glycol ester by reacting an olefin selected from the groups consisting of ethylene and propylene with molecular oxygen and a carboxylic acid selected from the groups consisting of fatty acids, dibasic carboxylic acids and olefinically unsaturated carboxylic acids in the presence of an effective amount of catalyst, the improvement which comprises: using a catalyst selected from the group consisting of a compound of the formula $Ti(OR^1)_m(OAc)_n$, where $R^1$ is alkyl of 1 to 20 carbon atoms, or a pair of $R^1$ radicals for an alkylene radical, $m$ and $n$ are integers from 1 to 3, the sum of $m + n$ being 4, and Ac is an acyl radical of a carboxylic acid of 1 to 20 carbon atoms, a compound of the formula $Ti(OR^1)_4$, where $R^1$ is alkyl of 1 to 20 carbon atoms, or one to two pairs of $R^1$ radicals form an alkylene radical of 2 to 20 carbon atoms, and a compound of the formula $Ti_2O(OAc)_6$, where Ac is an acyl radical of a carboxylic acid of 1 to 20 carbon atoms.

2. A process as set forth in claim 1, wherein $R^1$ is alkyl of 2 to 10 carbon atoms.

3. A process as set forth in claim 1, wherein Ac is acetyl.

* * * * *